United States Patent [19]

Webber

[11] 4,261,991
[45] Apr. 14, 1981

[54] **METHOD OF TREATING INFECTIONS CAUSED BY *STREPTOCOCCUS FAECALIS***

[75] Inventor: J. Alan Webber, Indianapolis, Ind.

[73] Assignee: Eli Lilly and Company, Indianapolis, Ind.

[21] Appl. No.: 35,035

[22] Filed: May 1, 1979

[51] Int. Cl.$^3$ .............................................. A61K 31/54
[52] U.S. Cl. ...................................... 424/246; 544/26
[58] Field of Search .......................................... 424/246

[56] References Cited

U.S. PATENT DOCUMENTS

| | | | |
|---|---|---|---|
| 3,335,136 | 8/1967 | Flynn | 424/246 |
| 3,907,784 | 9/1975 | Huffman | 424/246 |

*Primary Examiner*—Jerome D. Goldberg
*Attorney, Agent, or Firm*—William B. Scanlon; Arthur R. Whale

[57] ABSTRACT

7-(2,5-Dichloro or 3,4-dichlorophenyl) cephalosporanic acids or derivatives thereof in which the acetoxy group is replaced by hydroxyl or certain heterocyclic thio groups are useful in the treatment of infections caused by *Streptococcus faecalis*.

4 Claims, No Drawings

METHOD OF TREATING INFECTIONS CAUSED BY *STREPTOCOCCUS FAECALIS*

This invention relates to a method of treating a bacterial infection caused by strains of *Streptococcus faecalis* using certain 7-(dihalogenated phenylthioacetamido) cephalosporanic acids and derivatives thereof. Also contemplated are the novel compounds useful in said method.

In its process aspect, the invention sought to be patented comprehends a method or treating a bacterial infection caused by a strain of *Streptococcus faecalis* which comprises administering to a warm-blooded host afflicted with said infection an effective amount of a compound of the formula:

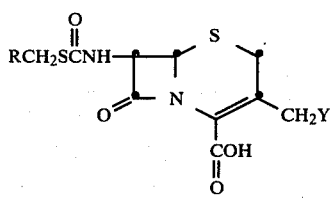

wherein R is 2,5-dichlorophenyl or 3,4-dichlorophenyl; and Y is hydroxy, acetoxy, or a heterocyclic thio moiety —S—X wherein X is a heterocyclic group of the formula

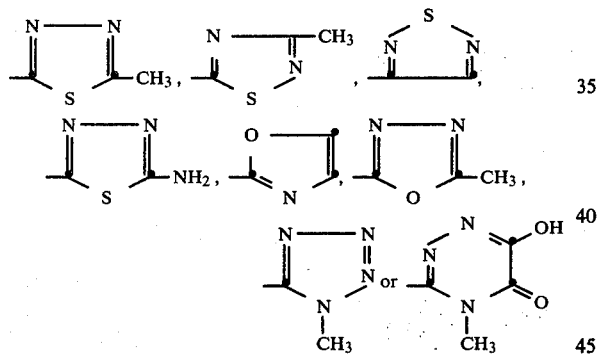

or a salt thereof with a non-toxic, pharmaceutically acceptable cation, provided that when R is 3,4-dichlorophenyl, Y cannot be hydroxy or acetoxy.

In subgeneric aspects, the invention includes the following embodiments:
(i) compounds of Formula I wherein R is 2,5-dichlorophenyl;
(ii) compounds of Formula I wherein R is 2,5-dichlorophenyl and Y is acetoxy;
(iii) compounds of Formula I wherein R is 2,5-dichlorophenyl and Y is a heterocyclic thio moiety as defined supra; and
(iv) compounds of Formula I wherein R is 3,4-dichlorophenyl and Y is a heterocyclic thio moiety as defined supra.

The compounds of Formula I are either known or are prepared by conventional methods from known intermediates. U.S. Pat. No. 3,335,135 describes the compounds of Formula I wherein R is 2,5-dichlorophenyl or 3,4-dichlorophenyl and Y is acetoxy. U.S. Pat. No. 4,056,676 describes the compound of Formula I wherein R is 2,5-dichlorophenyl or 3,4-dichlorophenyl and Y is acetoxy, 5-methyl-1,3,4-thiadiazol-2-ylthio, or 1-methyl-1H-tetrazol-5-ylthio.

The compounds of Formula I wherein Y is a heterocyclic thio group in general are prepared from a 7-(2,5- or 3,4-dichlorophenylacetamido)cephalosporanic acid by nucleophilic displacement of the acetoxy group by an appropriate heterocyclic thio group. This reaction can be performed in known manner, either in an aqueous medium by reacting a salt (e.g., sodium) of the desired cephalosporanic acid derivative with the sulfur nucleophile at pH 5-8 at an elevated temperature (35°-70° C.) (see, for example, U.S. Pat. No. 3,278,531 and J. Cocker et al., *J. Chem. Soc.*, 1965, 5015), or in an organic solvent under anhydrous conditions by reacting the cephalosporanic acid derivative with the sulfur nucleophile at an elevated temperature (50°-140° C.) (see, for example, U.S. Pat. No. 4,144,391.) Other methods of preparation can be employed, such as by N-acylating the appropriate 7-amino-3-[(heterocyclic)-methylthio]-3-cephem-4-carboxylic acid using methods conventional in the art of cephalosporin chemistry.

The compounds of Formula I may be utilized in their acid form or in the form of a salt formed by the reaction of the free carboxyl group with a suitable base. The base must have sufficient strength to neutralize the acid, and the cation derived from the base must be non-toxic and acceptable for pharmaceutical purposes. Suitable cations will be apparent to those skilled in the art. Examples are sodium, lithium, potassium, ammonium, and substituted ammonium (e.g., methyl ammonium or ethyl ammonium). Less soluble salts, e.g., calcium, barium, procaine, quinine, cyclohexylbis (methyl amine) or dibenzyl ethylene diamine salt, can also be employed.

In its composition of matter aspect, the invention contemplates the novel compounds of Formula I wherein R is 2,5-dichlorophenyl or 3,4-dichlorophenyl and Y is a heterocyclic thio moiety of the formula —S—X where X is a heterocyclic group of the formula:

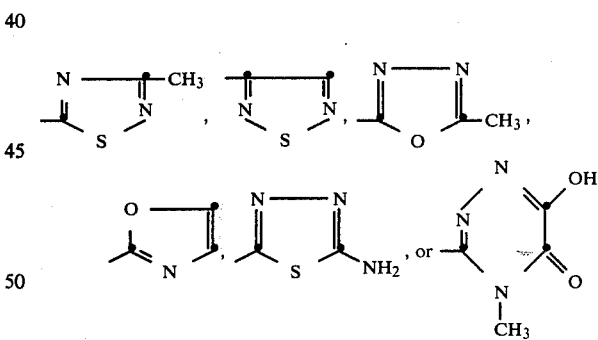

or a salt thereof with a non-toxic, pharmaceutically acceptable cation. In subgeneric aspects, the invention includes the following embodiments:
(i) the compound of Formula I wherein R is 2,5-dichlorophenyl; and
(ii) the compound of Formula I wherein R is 3,4-dichlorophenyl.

The compounds of Formula I are highly effective in inhibiting the growth of strains of *Streptomyces faecalis*, as evidenced by standard agar dilution susceptability tests. *Streptomyces faecalis* is classified as a species of Groups D β-hemolytic streptococci, also known as enterococci. Infections caused by Group D β-hemolytic streptococci, in particular *Streptomyces faecalis*, are generally known to be resistant to cephalosporin antibiotics. The infections caused by Group D streptococci commonly involve the endocardium (endocarditis), the urinary tract, the intestines, the biliary tract, postoperative wounds, and interabdominal abscesses. Endocarditis is clinically a very important disease and is frequently difficult to treat by antibiotic therapy. The disease is commonly treated by infusion of penicillin G in combination with streptomycin or vancomycin.

For the treatment of *Streptomyces faecalis* infections, a compound of Formula I is administered parenterally, preferably by intramuscular injection (IM) or intravenous injection (IV). The dose to be administered will depend on various factors including the size and age of the host, the nature and severity of the disease being treated, and the particular physical well-being of the individual patient. Generally, for a 70 kg host, the compound is administered in an amount from about 1 to about 12 g. per day (IV or IM). The effective amount of the compound can be administered in divided doses, e.g., 0.25 to 6 g. given two to four times each day.

Injectable formulations containing a compound of Formula I can be prepared in the same manner as with other injectable cephalosporins, and suitable aqueous formulations containing pharmaceutically acceptable excipients will be known to those skilled in the art.

The compounds of Formula I may be used in combination with other known antibiotic agents, such as streptomycin and vancomycin, and such use will be apparent to those skilled in the art.

The following examples are illustrative of the manner of making and using the tangible embodiments of this invention:

EXAMPLE 1

A mixture of 2,5-dichlorophenylthioacetic acid (2.37 g, 10 mM) and oxalyl chloride (5 ml.) in benzene (150 ml.), with one drop of dimethylformamide, is heated at 100° C. (steam bath) for one-half hour. Solvent is removed in vacuo leaving a residual oil. The oil, dissolved in acetone (50 ml.) is added dropwise at 0° to a solution of deacetyl 7-aminocephalosporanic acid (2.57 g., 11 mM) and sodium bicarbonate (NaHCO$_3$) (2.57 g.) in water (100 ml.) and acetone (50 ml.). The mixture is stirred for one hour, after which acetone is removed in vacuo (cold). The aqueous residue is added to ethyl acetate (100 ml.) at −10° C., and the mixture is stirred vigorously. The pH is adjusted to 2.5 with concentrated HCl. The mixture is quickly filtered. The filtrate is then separated into two phases. The aqueous phase is extracted with ethylacetate (50 ml.) and the organic phase is combined with the previous organic phase. The combined organic phases are dried over anhydrous Na$_2$SO$_4$, charcoal is added, and the mixture is allowed to remain one hour in the cold. The mixture is filtered through a talc pad and the filtrate is evaporated in vacuo. 7-[2-[(2,5-Dichlorophenyl)thio]acetamido]-3-hydroxymethyl-3-cephem-4-carboxylic acid is obtained as white crystals from the reduced solvent.

IR (Nujol moll): 1760 cm$^{-1}$ ($\beta$-lactam carbonyl); NMR (DMSOd$_6$): δ3.6 (2H, S, 2CH$_2$), 3.95 (2H, S, side chain CH$_2$), 4.35 (2H, S, 3—CH$_2$CH$_2$), 5.1 (1H, d, H$_6$), 5.7 (1H, d of d, H$_7$), 7.1–7.6 (3H, m, aromatic H), 9.3 (1H, d, amide NH); Titration: Mol. wt. 446.5 (Theory 449.3); $\lambda_{max}$=254 ($\epsilon$=16,000)

EXAMPLE 2

A mixture of 3-(acetoxymethyl)-7-[2-[(2,5-dichlorophenyl)thio]acetamido]-3-cephem-4-carboxylic acid, sodium salt [255 mg, 0.5 mM], 3-mercapto-1,2,5-thiadiazole, sodium salt (1 mM) and pH 6.4 phosphate buffer (20 cc) is heated for 8 hours at 65° C. Upon cooling, there is precipitated a cream-colored solid which is collected by filtration and dried. Yield of 7-[2-[(2,5-dichlorophenyl)-thio]acetamido]-3-[(1,2,5-thiadiazolyl)-thiomethyl]-3-cephem-4-carboxylic acid, as the sodium salt: 59 mg.

| Analysis | Theory | Found |
| --- | --- | --- |
| C | 37.83% | 33.16% |
| H | 2.29 | 2.46 |
| N | 9.80 | 9.63 |

UV Analysis $\lambda_{max}$=256 ($\epsilon$=17,600).

EXAMPLE 3

A mixture of 3-(acetoxymethyl)-7-[2-[(2,5-dichlorophenyl)thio]acetamido]-3-cephem-4-carboxylic acid (667 mg, 1.3 mM), 5-amino-1,3,4-thiadiazole-2-thiol (173 mg, 1.3 mM), sodium bicarbonate (109 mg, 1.3 mM), and pH 6.4 buffer (25 cc.) is heated at 65° C. for 8 hours. Upon cooling there is precipitated a solid which is collected by filtration and dried. Yield of 3-[(5-amino-1,3,4-thiadiazol-2-yl)thiomethyl]-7-[2-[(2,5-dichlorophenyl)thio]acetamido]-3-cephem-4-carboxylic acid, as the sodium salt: 240 mg.

| Analysis | Theory | Found |
| --- | --- | --- |
| C | 38.30% | 38.5% |
| H | 2.68 | 2.97 |
| N | 12.41 | 12.58 |

UV Analysis $\lambda_{max}$=255 ($\epsilon$=17,700).

EXAMPLE 4

A mixture of 3-acetoxymethyl-7-[2-[(2,5-dichlorophenyl)thio]acetamido]-3-cephem-4-carboxylic acid (513 mg, 1 mM), 2-mercapto-1,3-oxazole (126 mg, 1.25 mM), sodium bicarbonate (105 mg, 1.25 mM), and pH 6.4 buffer (25 cc.) is heated at 67° C. for 8 hours. After cooling, the mixture is extracted with ethyl acetate. The ethyl acetate extract is dried over magnesium sulfate and evaporated to dryness to afford a residue (577 mg) which is triturated with warm ethyl acetate to give 7-[2-[(2,5-dichlorophenyl)thio]acetamido]-3-[(2-oxazolyl)thiomethyl]-3-cephem-4-carboxylic acid, as the sodium salt. Yield: 118 mg of dried product.

| Analysis | Theory | Found |
| --- | --- | --- |
| C | 42.86% | 42.99% |
| H | 2.84 | 3.04 |
| N | 7.89 | 7.62 |

UV Analysis $\lambda_{max}$=255 ($\epsilon$=19,200).

EXAMPLE 5

A mixture of 3-acetoxymethyl-7-[2-[(2,5-dichlorophenyl)thio]acetamido]-3-cephem-4-carboxylic acid, sodium salt (513 mg. 1 mM), 3-mercapto-4,5-dihydro-6-hydroxy-4-methyl-5-oxo-as-triazine hydrate (221 mg., 1.25 mM), sodium carbonate (105 mg, 1.25 mM), and pH 6.4 buffer (25 cc.) is warmed with slow stirring. A homogeneous reaction mixture forms within one hour. The mixture is heated at 65° C. for 18 hours. Upon cooling there is formed a white solid which is collected by filtration and dried. Yield of 7-[2-[(2,5-dichlorophenyl)thio]acetamido]-3-[(4,5-dihydro-6-hydroxy-4-methyl-5-oxo-as-triazin-3-yl)thiomethyl]-3-cephem-4-carboxylic acid, as the sodium salt: 240 mg.

| Analysis | Theory | Found |
|---|---|---|
| C | 39.22% | 40.19% |
| H | 2.63 | 3.01 |
| N | 11.43 | 8.99 |

UV Analysis $\lambda_{max} = 254$ ($\epsilon = 21,600$).

EXAMPLE 6

A mixture of 3-acetoxy-7-[2-[(2,5-dichlorophenyl)thio]acetamido]-3-cephem-4-carboxylic acid, sodium salt (465 mg, 0.91 mM), 3-methyl-5-mercapto-1,2,4-thiadiazole (165 mg, 1.25 mM), sodium bicarbonate (105 mg, 1.25 mM), and pH 6.4 buffer (25 cc.) is heated at 65°–70° C. for 18 hours. Upon cooling, there is precipitated a solid which is collected by filtration and dried. Yield of 7-[2-[(2,5-dichlorophenyl)thio]acetamido]-3-[(3-methyl-1,2,4-thiadiazolyl)thiomethyl]-3-cephem-4-carboxylic acid, as the sodium salt: 180 mg.

| Analysis | Theory | Found |
|---|---|---|
| C | 38.98% | 40.95% |
| H | 2.58 | 3.23 |
| N | 9.57 | 7.01 |

EXAMPLE 7

A mixture of 3-acetoxymethyl-7-[2-[(2,5-dichlorophenyl)thio]acetamido]-3-cephem-4-carboxylic acid (1.54 g, 3 mM), 2-methyl-5-mercapto-1,3,4-oxadiazole (417 mg, 3.6 mM), sodium bicarbonate (303 mg., 3.6 mM) in water (20 ml.) is sonnicated and then heated for 30 minutes at 64° C. to afford a clear solution. The solution is cooled to room temperature, diluted with water (5 ml.), adjusted to pH 6.5 (from pH 6.0), and allowed to stir overnight at 63° C. Analysis of the reaction mixture by tlc on alumina gel using 10:3 ether—(3:1 acetic acid-water) after 18 hours showed streaking and one major spot. After 20 hours, the solution is cooled to room temperature. Ethyl acetate (40 ml.) is added, and the resulting mixture is cooled to 0° C. and adjusted to pH 2.4 (from pH 7.4) with 5% hydrochloric acid. The layers are separated. The aqueous layer is extracted once with ethylacetate. The ethyl acetate phases are combined, washed with water and saturated sodium chloride solution, and dried over anhydrous sodium sulfate. The sodium sulfate is removed by filtration and the solvent is removed by evaporation. Yield of yellow foam: 1.64 g.

The crude product is purified as follows: To a 300-mg. sample (0.547 mM), dissolved in 8 ml. of methanol, is added dropwise 0.55 ml. of 1 M lithium acetate. The solution is "scratched" and placed in a refrigerator overnight. The precipitate which forms is collected, washed with ether, and dried. Yield of 7-[2-[(2,5-dichlorophenyl)thio]acetamido]-3-[(5-methyl-1,3,4-oxadiazol-2-yl)thiomethyl]-3-cephem-4-carboxylic acid, as the lithium salt: 172 mg.

| Analysis | Theory | Found |
|---|---|---|
| C | 41.23% | 40.22% |
| H | 2.73 | 3.26 |
| N | 10.12 | 7.01 |
| Cl | 12.81 | 12.11 |
| S | 17.38 | 12.32 |

UV Analysis $\lambda_{max} = 253$ ($\epsilon = 14,278$)

EXAMPLE 8

The in vitro activities of representative compounds of Formula I are assessed and demonstrated by the agar dilution method. The results are shown in Table 1 where the activity is measured by the MIC values, defined as the concentration of the compound capable of inhibiting the growth of the test organism.

TABLE 1

In Vitro Antibacterial Activity Against Eleven Strains of *Streptococcus faecalis*

$$\text{RSCH}_2\text{CNH}-\underset{O}{\overset{O}{\|}}\text{-cephem structure with } \text{CH}_2\text{Y, CO}_2\text{H} \qquad I$$

| R | Y | MIC μg/ml* |
|---|---|---|
| 2,5-diCl phenyl | -S-[thiadiazole with CH3] | 1.29 |
| 2,5-diCl phenyl | -S-[thiadiazole] | 1.37 |
| 2,5-diCl phenyl | -S-[thiadiazole with CH3] | 1.88 |
| 2,5-diCl phenyl | -S-[oxazole] | 1.88 |
| 2,5-diCl phenyl | $-O-\overset{O}{\overset{\|}{C}}CH_3$ | 2.00 |
| 2,5-diCl phenyl | -S-[oxadiazole with CH3] | 2.13 |
| 2,5-diCl phenyl | -S-[triazole with N-CH3] | 3.11 |
| 2,5-diCl phenyl | —OH | 3.11 |
| 2,5-diCl phenyl | -S-[pyrazine with OH, N-CH3] | 3.76 |

TABLE 1-continued

In Vitro Antibacterial Activity Against Eleven Strains of *Streptococcus faecalis*

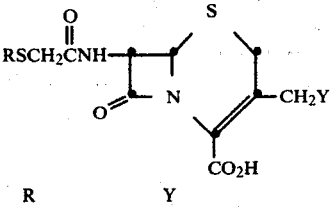

| R | Y | MIC μg/ml* |
|---|---|---|
| 2,5-diCl phenyl | 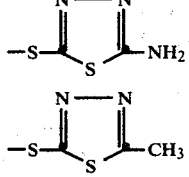 | 4.26 |
| 3,4-diCl phenyl |  | 1.76 |
| 3,4-diCl phenyl | 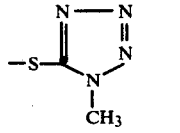 | 4.83 |

*Geometric mean MIC as determined by the tube dilution method against eleven strains of *Streptococcus faecalis*.

What is claimed is:

1. A method of treating a bacterial infection caused by a strain of *Streptococcus faecalis* which comprises parenterally administering to a host afflicted with said infection an effective amount of the compound 7-[2[(2,5-dichlorophenyl)thio]acetamido]-3-[(2-amino-1,3,4-thiadiazol-5-yl)thiomethyl]-3-cephem-4-carboxylic acid.

2. A method for treating a bacterial infection caused by a strain of *Streptococcus faecalis* which comprises parenterally administering to a host afflicted with said infection an effective amount of the compound 7-[2[(2,5-dichlorophenyl)thio]acetamido]-3-(2-oxazolyl)-thiomethyl-3-cephem-4-carboxylic acid.

3. A method of treating a bacterial infection caused by a strain of *Streptococcus faecalis* which comprises parenterally administering to a host afflicted with said infection an effective amount of the compound 7-[2-[(2,5-dichlorophenyl)thio]acetamido]-3-(2-methyl-1,3,4-oxadiazol-5-yl)thiomethyl-3-cephem-4-carboxylic acid.

4. A method of treating a bacterial infection caused by a strain of *Streptococcus faecalis* which comprises parenterally administering to a host afflicted with said infection an effective amount of the compound 7-[2[(2,5-dichlorophenyl)thio]acetamido]-3-(4,5-dihydro-6-hydroxy-4-methyl-5-oxo-as-triazin-3-yl)thiomethyl-3-cephem-4-carboxylic acid.

* * * * *